United States Patent
Boyer

(10) Patent No.: US 7,476,637 B1
(45) Date of Patent: Jan. 13, 2009

(54) COATED CATALYST FOR AROMATIC ALKYLATION

(75) Inventor: Christopher C. Boyer, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 11/780,250

(22) Filed: Jul. 19, 2007

(51) Int. Cl.
*B01J 29/06* (2006.01)

(52) U.S. Cl. ............................. 502/60; 502/63; 502/64; 502/68; 502/69; 502/71; 502/77; 502/79; 502/84

(58) Field of Classification Search .................. 502/60, 502/63, 64, 68, 69, 71, 77, 79, 80, 84
See application file for complete search history.

(56) References Cited

U.S. PATENT DOCUMENTS

| | | | |
|---|---|---|---|
| 2,860,173 A | 11/1958 | Jones et al. | |
| 4,215,011 A | 7/1980 | Smith, Jr. | |
| 4,232,177 A | 11/1980 | Smith, Jr. | |
| 4,242,530 A | 12/1980 | Smith, Jr. | |
| 4,250,052 A | 2/1981 | Smith, Jr. | |
| 4,302,356 A | 11/1981 | Smith, Jr. | |
| 4,307,254 A | 12/1981 | Smith, Jr. | |
| 4,443,559 A | 4/1984 | Smith, Jr. | |
| 4,849,569 A | 7/1989 | Smith, Jr. | |
| 4,891,458 A | 1/1990 | Innes et al. | |
| 4,950,834 A | 8/1990 | Arganbright et al. | |
| 5,019,669 A | 5/1991 | Adams et al. | |
| 5,043,506 A | 8/1991 | Crossland | |
| 5,055,627 A | 10/1991 | Smith, Jr. et al. | |
| 5,086,193 A | 2/1992 | Sy | |
| 5,176,883 A | 1/1993 | Smith, Jr. et al. | |
| 5,215,725 A | 6/1993 | Sy | |
| 5,243,115 A | 9/1993 | Smith, Jr. et al. | |
| 5,321,181 A | 6/1994 | Smith, Jr. et al. | |
| 5,770,782 A | 6/1998 | Knifton et al. | |
| 2006/0281828 A1* | 12/2006 | Nakayama et al. | ............ 522/71 |

* cited by examiner

*Primary Examiner*—Elizabeth D Wood
(74) *Attorney, Agent, or Firm*—Osha Liang LLP

(57) ABSTRACT

A catalyst useful for multi-phase reactors that includes an active component surrounded by a coating on a surface of the active component, wherein the coating provides a liquid film around the active component to increase the useful life of the active component as compared to an uncoated active component.

10 Claims, 1 Drawing Sheet

COATED CATALYST FOR AROMATIC ALKYLATION

BACKGROUND OF INVENTION

1. Field of the Invention

Embodiments disclosed herein relate to catalysts useful for the alkylation of aromatic compounds. More particularly, embodiments relate to catalysts having lower deactivation rates during use. Still more particularly, embodiments relates to an extruded zeolite catalyst which has an inert, porous coating that maintains a liquid phase within the pores of the catalyst.

2. Background Art

The alkylation of aromatic compounds with olefins is an established commercial having 2 to about 6 carbon atoms) has value as a gasoline octane enhancer. Light aromatic compounds alkylated with longer chain (that is, having greater than about 8 to 10 carbon atoms) linear olefins are commonly sulfonated to produce surfactants suitable for use in detergent manufacture.

The alkylation of benzene and other light aromatic compounds has typically been carried out using hydrofluoric acid or a solid acid catalyst in a fixed bed, plug flow process. For example, U.S. Pat. No. 2,860,173 discloses the use of a solid phosphoric acid as a catalyst for the alkylation of benzene with propylene to produce cumene. More recently, the use of Friedel Crafts catalysts, especially aluminum chloride and certain natural zeolites and synthetic commercial sieves, as alkylation catalysts has been taught.

Still more recently, alkylation of benzene and light aromatics with $C_6/C_{30}$ olefin co-fed with the aromatics over a solid catalyst bed in a reactive distillation column has been carried out in a reactive distillation column (U.S. Pat. No. 5,770,782).

Solid acid alkylation catalysts tend to deactivate rapidly in the presence of dialkylated aromatic products. Carbonaceous deposits and heavy organics build up on the catalyst surface, with a resultant decrease in catalyst effectiveness and a need to shut the process down to regenerate the catalyst. This tends to be related to the exothermic nature of the reaction, which has a tendency to be severe and difficult to control.

Regeneration is typically provided using benzene maintained in the liquid phase at a pressure of at least 500 psig and temperatures in excess of 250° C. Ethyl benzene and cumene have traditionally been produced by the reaction of benzene and the respective olefin, i.e., ethylene and propylene in the presence of an acidic catalyst. In some known processes, the catalyst is highly corrosive and has a relatively short life, e.g., $AlCl_3$, $H_3PO_4$ on clay, $BF_3$ on alumina, and others require periodic regeneration, e.g., molecular sieves. The exothermicity of the reaction and the tendency to produce polysubstituted benzene require low benzene conversions per pass with large volume recycle in conventional processes.

Recently a method of carrying out catalytic reactions has been developed, wherein the components of the reaction system are concurrently separable by distillation, using the catalyst structures as the distillation structures. Such systems have been applied to aromatic alkylation as in U.S. Pat. Nos. 4,950,834; 4,849,159; 5,019,669; 5,043,506; 5,055,627; 5,086,193; 5,176,883; 5,215,725; 5,243,115; and 5,321,181. A catalyst/distillation structure described is a cloth belt with a plurality of pockets spaced along the belt, which is then wound in a helix about a spacing material such as stainless steel knitted mesh. These units are then disposed in the distillation column reactor. These patents all specifically disclose the use of A, X, Y, L, erionite, omega, mordenite, and beta zeolites as the catalyst in the catalytic distillation structure. In addition, U.S. Pat. No. 4,443,559 discloses a variety of catalyst structures for this use and is incorporated herein.

Zeolites normally foul rapidly in the presence of olefin vapors during the alkylation of benzene. This shortens the catalyst life in service for producing alkyl aromatics, i.e., ethyl benzene (EB), cumene and butylbenzene. One solution to this has been to operate such that the catalyst is always immersed in a liquid phase as in U.S. Pat. No. 4,891,458. Catalyst stability is a major component of advancing benzene alkylation technology. The prior structures disclosed in U.S. Pat. Nos. 4,215,011; 4,232,177; 4,242,530; 4,250,052; 4,302,356; and 4,307,254 presumably provided a barrier between the catalyst and the vapor phase olefin. This mass transfer barrier also lowered the effective catalyst activity. Using the catalyst in wire mesh structure triples the catalyst mass activity. However, the catalyst rapidly deactivates: $(k/ko \sim exp[-0.003\ t(hr)])$.

In one commercial process, a fixed bed reactor operates in liquid phase with olefin content below the liquid saturation level, which increases process costs. In another commercial process, a multi-phase reactor operates with the catalyst enclosed in liquid filled fiberglass bags, which introduces a liquid film through which the olefin must pass to get to the catalyst and mass transfer limitations slow the reaction rate.

What is still needed therefore, are methods and catalysts that can provide increased run times, while maintaining useful activity rates.

SUMMARY OF INVENTION

In one aspect, a catalyst useful for multi-phase reactors comprising an active component surrounded by a coating on a surface of the active component, wherein the coating provides a liquid film around the active component to increase the useful life of the active component as compared to an uncoated active component.

Other aspects and advantages of the invention will be apparent from the following description and the appended claims.

DETAILED DESCRIPTION

Figure 1:
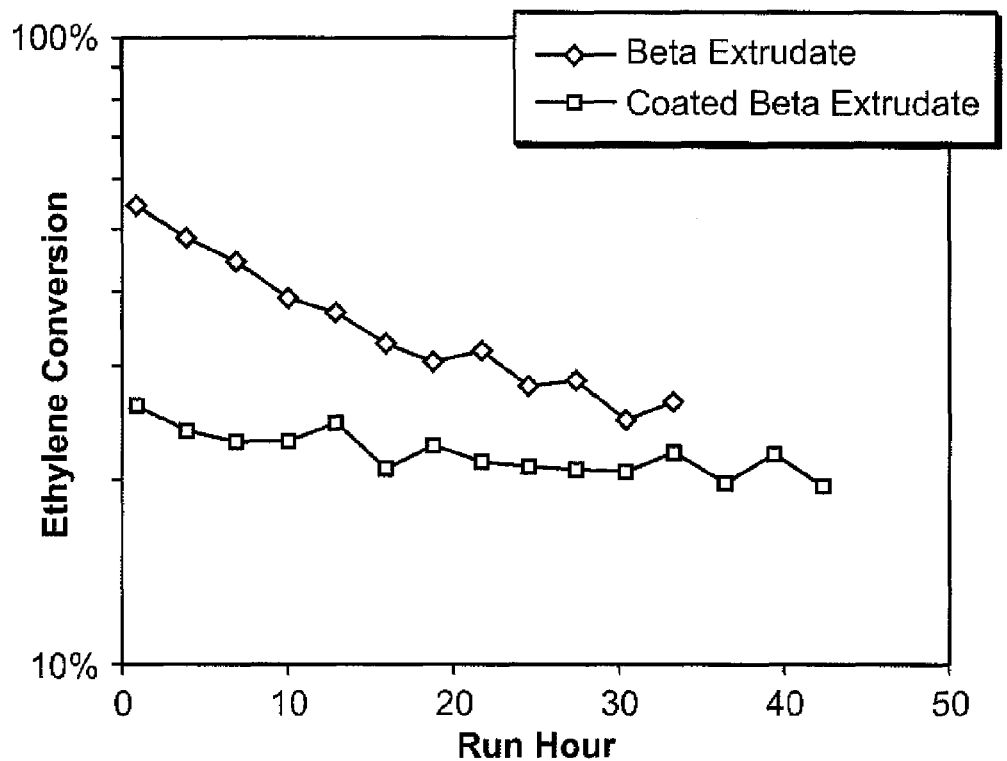
FIG. 1 is a graphical presentation of the ethylene conversion versus run time for a catalyst in accordance with one embodiment as compared to standard catalyst (uncoated).

Embodiments disclosed herein provide a method to protect the active sites of an active component, i.e., the catalyst. Specifically, embodiments herein disclose the use of an inert, porous coating located on the outer surface of a catalyst to maintain a liquid film around the active portion of the catalyst such that the active sites will not come into contact with the vapor phase (generally the olefin).

This inert, porous coating has surface properties and a pore size such that capillary pressure maintains liquid in the pores. Liquid that becomes trapped in the inert, outer coating prevents the gas phase from direct contact with the active sites of the catalysts. The catalyst can be subjected to multi-phase flow, and can be used in a process with a cost advantage.

Embodiments of the present invention may involve the use of the protected catalyst in an aromatic alkylation process.

For example, the aromatic alkylation process may involve a catalytic distallation process and comprise a continuous, pressurized process using a distillation column configuration and system including a reactive zone, a first rectification zone at the top of the distillation column for rectification and recovery of unreacted aromatic hydrocarbon feedstock, an intermediate reactive zone containing a solid acid alkylation catalyst, and a second rectification zone (or stripping zone) positioned below and in communication with the reactive zone, where unreacted aromatic hydrocarbon and olefin feedstock may be separated from the alkylation product and any by-products. Below the second rectification zone is a reboiler and means for withdrawing the alkylation product from the column. Suitably positioned injectors allow for the controlled introduction of aromatic hydrocarbon compounds and olefin feedstock.

In one embodiment of a catalytic distallation alkylation process, at least a portion of a suitable aromatic feedstock is introduced at a point between the intermediate catalyst zone and the upper rectification zone, and at least a portion of a suitable olefin hydrocarbon feedstock is introduced at a point between the catalyst zone and a second, lower, rectification zone, and the aromatic hydrocarbon is passed through the catalyst zone to contact and react with the olefin feedstock in a counter-current, liquid phase reaction. In such an exemplary system, the conditions of the reaction require that the internal pressure in the reactive zone is maintained above about 1 atmosphere, preferably between about 20 and about 200 psig, and the combination of olefin and aromatic hydrocarbon in the reboiler maintained such that the temperature in the reboiler stays below the thermal degradation temperature for the alkylated product, which is about 265° C., and the molar ratio of the aromatic hydrocarbon to the olefin in the liquid phase can be maintained between about 3/1 to about 10/1, preferably between about 4/1 to about 8/1.

Those having ordinary skill in the art will appreciate that the above description is merely representative of applications in which the protective coating for the catalyst may be employed.

The alkylation reaction takes place primarily in the liquid phase on the solid catalyst in the reactive zone. Catalysts that may be used in embodiments disclosed herein include such acid zeolitic materials as W-Zeolite, beta-zeolite, acidic mordenite, acid clays, such as montmorillonite and medium pore zeolites such as ZSM-5, ZS M-12, ZSM-18, ZSM-20, MCM-22, and BETA, L, Y, mordenite, as well as rare earth exchanged forms or de-aluminated forms of the listed zeolites. Other catalysts that may be used include the fluorided versions of the above-mentioned zeolites and aluminum chloride impregnated on alumina, clays and silica-alumina.

The catalyst may be maintained in place by supporting it on structured packing, such as Koch-Glitch KATAMAX brand catalytic structured packing, or alternatively arranged in other ways familiar to those skilled in this art, for example, in a series of beds on perforated trays or in beds positioned in the liquid down corners of a trayed distillation column. The structured packing may also be used in the rectification zones, without catalyst, to improve the evaporation and condensation efficiency in those zones. In some embodiments, the catalyst/distillation structure may include the structures described above, such as a cloth belt with a plurality of pockets spaced along the belt, which is then wound in a helix about a spacing material such as stainless steel knitted mesh.

As noted above, embodiments disclosed herein comprise an active component (the catalytic material) surrounded by an inert, porous coating on the surface of the active component, wherein said inert, porous coating being characterized as having liquid capillary pressure, calculated by the formula:

$$Pc = 2\sigma \cos \theta / r$$

where: $Pc$ is the capillary pressure, psi; $\sigma$ is the surface tension of the liquid, pounds per cubic inch; $\theta$ is the contact angle of the porous coating in radians; and $r$ is the radius of the pore, inches.

In specific embodiments, the capillary pressure as calculated is at least 0.5 psi, and in yet other embodiments the capillary pressure is above 1 psi.

The capillary pressure must be sufficient to prevent the liquid from being displaced by vapor during two phase flow over the surface of the catalyst. For a given system, the material for the inert porous coating should be selected such that the contact angle is as small as possible (process liquid-phillic). The surface tension of the liquid will be fixed and low if operating at the bubble point.

It is preferable that pore size be small enough to maintain sufficient capillary pressure while as large as possible to minimize mass transfer resistance. The porosity should be as high as possible to minimize mass transfer resistance, but low enough so that the inert, porous coating has sufficient mechanical strength. The thickness of the inert coating should be minimized to reduce mass transfer resistance, but thick enough to provide a stable liquid layer around the active component and have a thickness of sufficient mechanical strength.

The preferred catalysts for the reactions are acidic molecular sieves. Molecular sieves are porous crystalline, three dimensional alumina silicates of the zeolite mineral group. The crystal skeleton is composed of silicon and aluminum atoms each surrounded by four oxygen atoms to form a small pyramid or tetrahedron (tetrahedral coordination). The term molecular sieve can be applied to both naturally occurring zeolites and synthetic zeolites. Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e., in so far as the natural zeolites are the functional equivalents to the synthetic zeolites.

Usually synthetic zeolites are prepared in the sodium form, that is, with a sodium cation in close proximity to each aluminum tetrahedron and balancing its charge. The principal types of molecular sieves have been reported, A, X, Y, L, erionite, omega, mordenite and beta.

Exemplary inert coatings that may be used in embodiments of the present invention include silica, alumina, clay, activated carbon and oxides of the metals of Groups 2, 13 and 14 of the IUPAC Standard periodic table. Combinations of one or more layers may be used. Those having ordinary skill in the art will appreciate that a number of other coatings may be used, so long as they have the requisite liquid capillary pressures.

The temperature in the reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus controlled by the pressure; by increasing the pressure, the temperature in the system is increased, and vice versa. It can also be appreciated that in catalytic distillation as in any distillation there is both a liquid phase (internal reflux) and a vapor phase. Thus, the reactants are partially in liquid phase which allows for a more dense concentration of molecules for reaction, whereas, the concurrent fractionation separates product and unreacted materials, providing the benefits of a liquid phase system (and a vapor phase system) while avoiding the detriment of having all of the components of the reaction system continually in contact with the catalyst which would limit the conversion to the equilibrium of the reaction system components.

The alkylation reaction can be carried out at sub-through super-atmospheric pressure, e.g., 0.20 to 40 atmospheres. The temperature will vary depending on the reactants and product. Furthermore, the temperature along the column will be as in any distillation column, i.e., the highest temperature will be in the bottom and the temperature along the column will be the boiling point of the compositions at that point in the column under the particular conditions of pressure. Moreover, the exothermic heat of reaction does not change the temperature in the column, but merely causes more boil up. However, the temperatures within the column with the above considerations in mind will generally be in the range of 10° C. to 260° C. (50° F. to 500° F.), preferably 21° C. to 260° C. (70° F. to 500° F.), and more preferably in the range of about 26° C. to 149° C. (80° F. to 300° F.) at pressures of 0.5 to 20.3 bar (0.5 to 20 atmospheres).

The olefins may be $C_2$ to $C_{20}$ olefins, preferably $C_2$ to $C_{12}$ olefins, including normal and branched forms thereof. For example, suitable olefins are ethylene, propylene, butylene, isobutylene, 1 pentene, 1 hexene, 2 hexene, 2,3 dimethyl 1 pentene, 1 octene, diisobutylene, 1 nonene and 1 decene, dodecene and the like.

The organic aromatic compounds are preferably those having a boiling point of 250° C. or less under the pressure conditions of the distillation column reactor. The organic aromatic compounds include hydrocarbons of one or more rings and 6 to 20 carbon atoms which may contain substituents which do not interfere with the alkylation including halogen (Cl, Br, F, and I), OH and alkyl, cycloalkyl, aralkyl and alkaryl radicals of 1 to 10 carbon atoms. Suitable organic aromatic compounds include benzene, xylene, toluene, phenol, cresol, ethyl benzene, diethyl benzene, naphthalene, indene, phenyl bromide, 1-bromo-2-chlorobenzene, 1-bromo-4 cyclohexyl benzene, 2 bromo-1,4 dihydroxy benzene, 1-(bromomethyl) naphthalene, 1,2 dihydronaphthalene and the like. A preferred group of compounds for use in the present process is benzene, xylene, toluene, phenol, and cresol.

The mole ratio of organic aromatic compound to olefin may be in the range of 2 to 100:1, preferably 2 to 50:1 and more desirably about 2 to 10:1. Selectivity to the monosubstituted product is improved with a greater excess of organic aromatic compound. Alkylation is forced to completion, since the simultaneous and concurrent fractionation and removal of the alkylation product from the distillation column reactor does not allow the products to contribute to the reverse reaction (Le Chatelier's Principle). However, very large molar excesses of organic aromatic compounds require a very high reflux ratio, and a low unit productivity. Hence, the correct ratio of organic aromatic compound to olefin must be determined for each combination of reactants as well as the acceptable olefin content in either the overhead or alkylation product (as described above). In a particular embodiment which is of current commercial importance, ethylene or propylene is reacted with benzene according to the present invention to form ethyl benzene or cumene, respectively.

For benzene alkylation, zeolite beta catalyst may be used in the form of 1.6 mm extrudates. The capillary pressure should be about 1 psi. The inert, porous coating may comprise silica, clay, activated carbon, or metal oxides. The inert, porous coating thickness should be between 0.01 and 1 mm, preferably less than 1 mm. The porosity should be about 50% and the pore size should be 0.01 to 1.5 μm, preferably about 0.8 μm.

EXAMPLE

Figure 2:
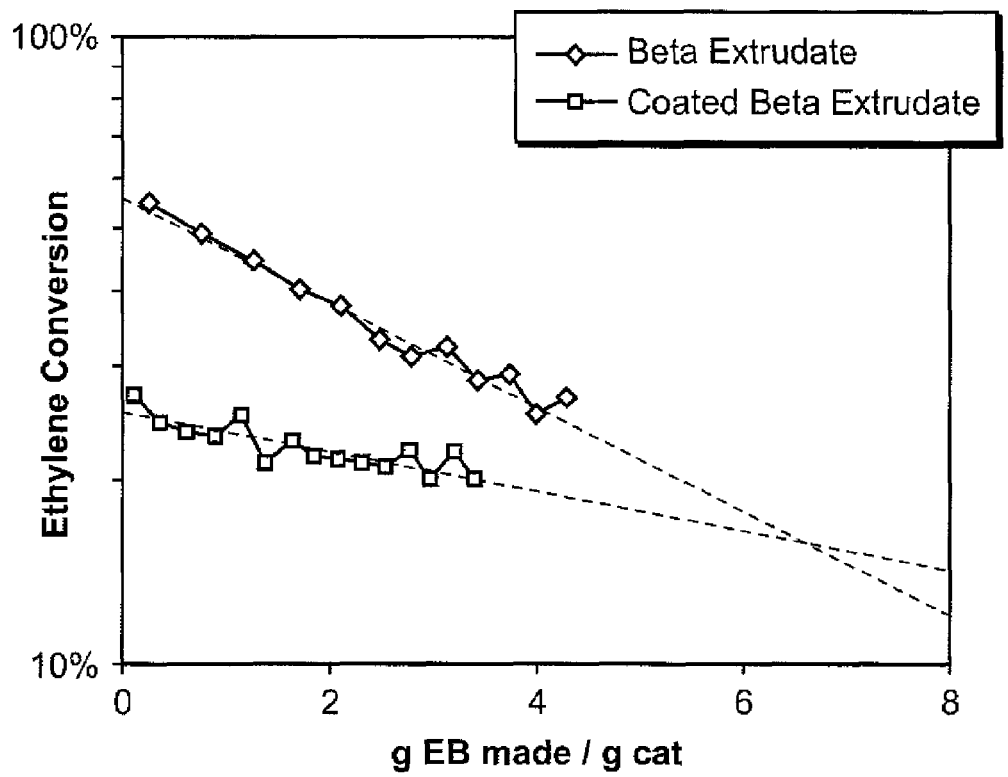
FIG. 2 is a graphical presentation of the ethylene conversion as a function of ethyl benzene production for a catalyst in accordance with an embodiment as compared to standard catalyst (uncoated).

A zeolite beta catalyst with a MgO coating of 100 to 500 μm was supplied by Zeolyst International and 0.55 grams of the catalyst diluted with SiO to a volume of about 4 ml was loaded into a reactor. Benzene with 0.647 wt. % ethylene was fed to the reactor. The reactor was operated at 204° C. (400° F.), 21.7 bar (300 psig) and a weight hourly space velocity of 522. An online gas chromatograph analyzed the product from the reactor. For comparison a standard zeolite beta catalyst of the same type as supplied by Zeolyst International was run under similar conditions. The results are shown in FIGS. 1 and 2.

Although the coated catalyst had a much lower activity, it had a much lower rate of deactivation, as demonstrated in the figures. Optimization of the inert, porous coating is expected to improve the activity. The experiment shows that by coating the catalyst the initial deactivation of the catalyst is reduced markedly. Additionally, although run duration for the experiments was limited, it is expected that activity of the uncoated catalyst will decrease and that activity of the coated catalyst will exceed that of the uncoated catalyst for an extended period of time.

Advantageously, embodiments of the present invention may provide one or more of the following benefits: a reactor with this catalyst can operate with a higher partial pressure of the reactive gas; multi-phase reactors can be packed such that both the liquid and vapor phases can contact the catalyst; catalyst life will be increased; the catalyst will be more robust against process upsets; and/or the composition of the inner, active component may be adjusted for increased activity (less binder), since the outer inert, porous coating can make up for the mechanical integrity of the catalyst particle.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed:

1. A catalyst useful for multi-phase reactors comprising:
an active component surrounded by an inert, porous coating on a surface of the active component, wherein the inert, porous coating provides a liquid film around the active component to increase the useful life of the active component as compared to an uncoated active component;
wherein said inert, porous coating has a pore diameter and contact angle which are selected in conjunction with the surface tension of the liquid to maintain a capillary pressure high enough to prevent the liquid from being displaced by vapor during a two phase flow over the catalyst;
wherein the capillary pressure is calculated by the formula Pc=2σ cos θ/r; where Pc is the capillary pressure, psi;

σ is the surface tension of the liquid, pounds per cubic inch;

θ is the contact angle of the inert, porous coating in radians; and r is the radius of the pore, inches.

2. The catalyst according to claim 1, wherein the capillary pressure as calculated is at least 0.5 psi.

3. The catalyst according to claim 1, wherein the capillary pressure as calculated is above 1 psi.

4. The catalyst according to claim 1, wherein the coating is selected from the group consisting of silica, alumina, clay, activated carbon and oxides of the metals of Groups 2, 13 and 14 of the IUPAC Standard periodic table.

5. The catalyst according to claim 1, wherein said active component comprises a zeolite.

6. The catalyst according to claim 1, wherein the active component is zeolite beta and the inert, porous coating is selected from the group consisting of silica, alumina, clay, activated carbon and other metal oxides.

7. The catalyst according to claim 1, for the alkylation of benzene to produce ethyl benzene comprising zeolite beta extrudates about 1.6 mm in diameter coated with an inert, porous coating about 0.1-1.0 mm thick, said inert, porous coating having a porosity of about 50% and a pore size of about 0.01-1.5 μm to produce a capillary pressure within the coating pores of about 1 psi.

8. A catalyst useful for multi-phase reactors comprising an active component surrounded by an inert, porous coating on the surface of the active component, said inert, porous coating is characterized as having liquid capillary pressure, calculated by the formula Pc=2σ cos θ/r where Pc is the capillary pressure, psi;

σ is the surface tension of the liquid, pounds per cubic inch;

θ is the contact angle of the inert, porous coating in radians; and r is the radius of the pore, inches;

wherein the capillary pressure as calculated is at least 0.5 psi.

9. The catalyst according to claim 8, wherein the pore diameter and contact angle of the inert, porous coating are selected in conjunction with the surface tension of the liquid in the reactor to maintain a capillary pressure high enough to prevent the liquid from being displaced by vapor during two phase flow over the catalyst.

10. The catalyst according to claim 8, wherein the active component is zeolite beta and the inert, porous coating is selected from the group consisting of silica, alumina, clay, activated carbon and other metal oxides.

* * * * *